US011547631B2

(12) United States Patent
Maritan et al.

(10) Patent No.: US 11,547,631 B2
(45) Date of Patent: Jan. 10, 2023

(54) PACKAGING DEVICE AND METHOD FOR REMOVING MEDICAL CONTAINERS FROM SAID PACKAGING DEVICE

(71) Applicant: Becton Dickinson France, Le Pont de Claix (FR)

(72) Inventors: Lionel Maritan, Pierre-Chatel (FR); Thomas Virot, Herbeys (FR)

(73) Assignee: Becton Dickinson France, Le Pont de Claix (FR)

( * ) Notice: Subject to any disclaimer, the term of this patent is extended or adjusted under 35 U.S.C. 154(b) by 302 days.

(21) Appl. No.: 16/652,792

(22) PCT Filed: Oct. 2, 2018

(86) PCT No.: PCT/EP2018/076818
§ 371 (c)(1),
(2) Date: Apr. 1, 2020

(87) PCT Pub. No.: WO2019/068723
PCT Pub. Date: Apr. 11, 2019

(65) Prior Publication Data
US 2020/0253824 A1     Aug. 13, 2020

(30) Foreign Application Priority Data
Oct. 2, 2017   (EP) ...................................... 17306313

(51) Int. Cl.
*A61J 1/16*       (2006.01)
*A61M 5/00*      (2006.01)
*B65D 25/10*    (2006.01)
(52) U.S. Cl.
CPC ................ *A61J 1/16* (2013.01); *A61M 5/002* (2013.01); *B65D 25/108* (2013.01)

(58) Field of Classification Search
CPC . A61J 1/16; A61M 5/00; A61M 5/002; B65D 25/10; B65D 25/108; B65D 75/34; B65D 77/04
(Continued)

(56) References Cited

U.S. PATENT DOCUMENTS 3,074,540 A * 1/1963 Beich ..................... B65D 75/36
                                                                206/469
5,048,684 A * 9/1991 Scott ..................... A61M 5/002
                                                              206/459.5
(Continued)

FOREIGN PATENT DOCUMENTS

CN        104609049 A        5/2015
EP          0439740 A1        8/1991
(Continued)

*Primary Examiner* — Bryon P Gehman
(74) *Attorney, Agent, or Firm* — The Webb Law Firm

(57) ABSTRACT

A packaging device is configured to support medical containers, the packaging device including a first nest including a first set of supporting units configured to support a proximal end of a first plurality of medical containers and a second nest including a second set of supporting units configured to support a proximal end of a second plurality of medical containers. The first set of supporting units and the second set of supporting units being configured to maintainer the first plurality of medical containers and the second plurality of medical containers in an inverted position relative to each other. The first nest further comprises apertures configured to maintain a distal end of the second plurality of medical containers while the second nest comprises apertures configured to maintain a distal end of the first plurality of medical containers.

19 Claims, 10 Drawing Sheets

(58) Field of Classification Search
USPC .................................. 206/366, 370, 446
See application file for complete search history.

(56) References Cited

U.S. PATENT DOCUMENTS

| | | | |
|---|---|---|---|
| 9,862,519 B2* | 1/2018 | Deutschle | ............... B65B 3/003 |
| 2009/0288977 A1 | 11/2009 | Vanderbush et al. | |
| 2015/0166217 A1 | 6/2015 | Deutschle et al. | |

FOREIGN PATENT DOCUMENTS

| | | | |
|---|---|---|---|
| EP | 2868593 | A1 | 5/2015 |
| GB | 772105 | | 4/1957 |
| JP | 10114369 | A | 5/1998 |
| JP | 200085753 | A | 3/2000 |

* cited by examiner

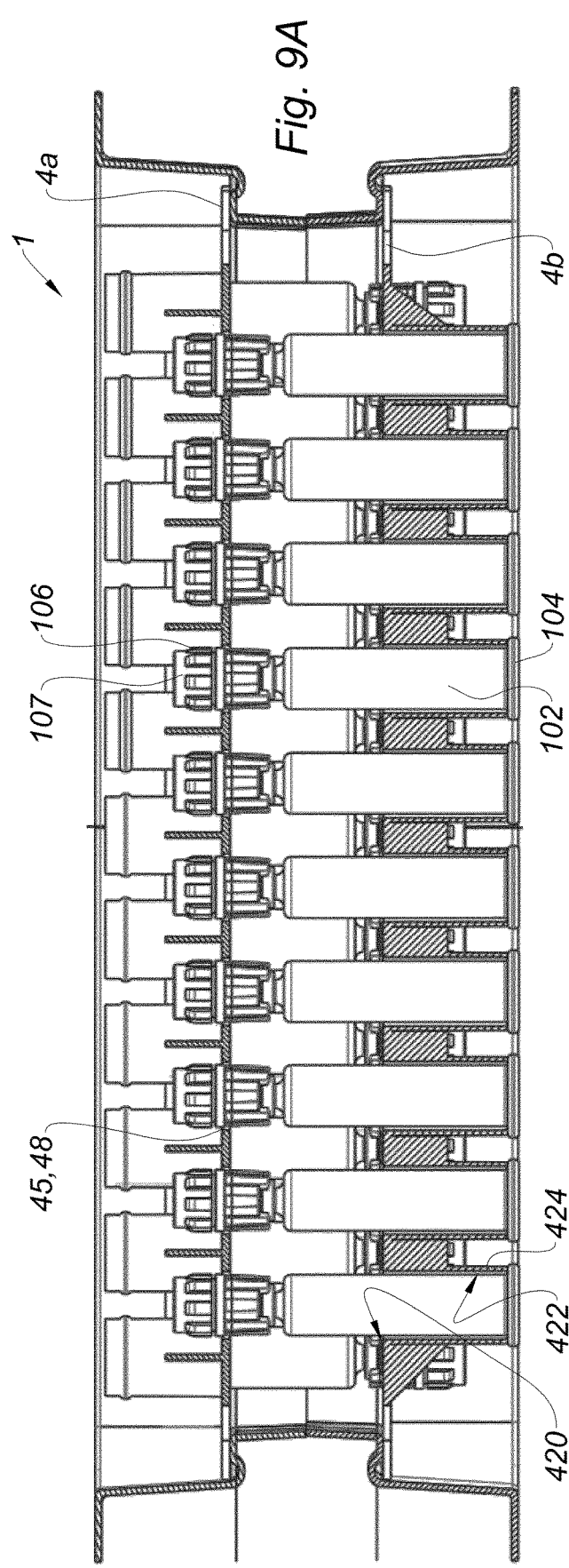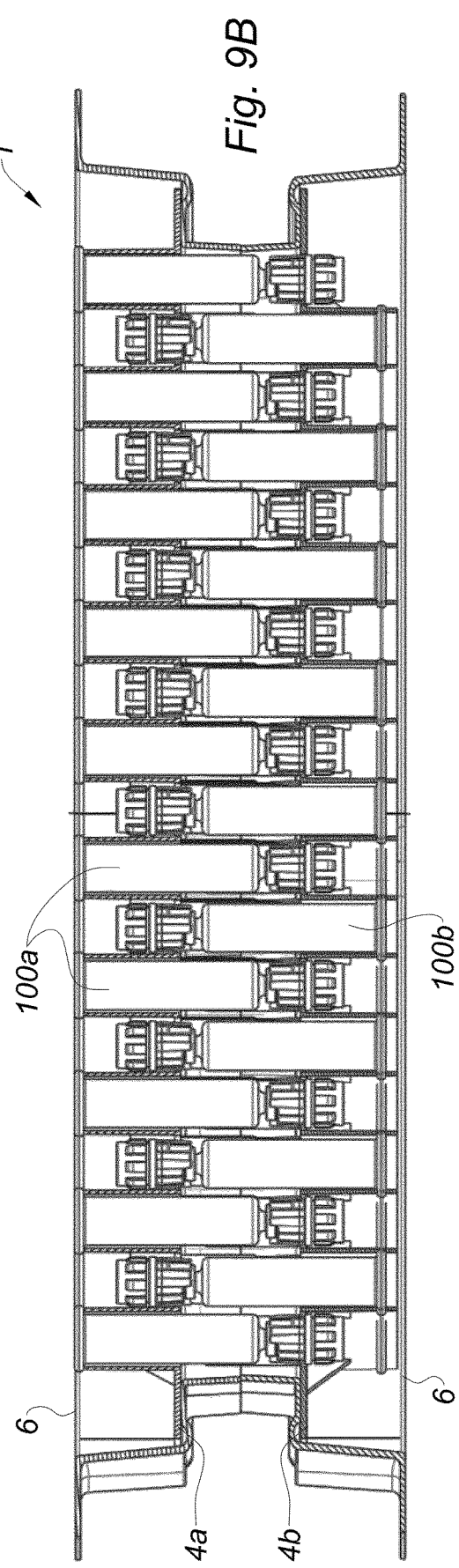

PACKAGING DEVICE AND METHOD FOR REMOVING MEDICAL CONTAINERS FROM SAID PACKAGING DEVICE

CROSS-REFERENCE TO RELATED APPLICATIONS

This application is the United States national phase of International Application No. PCT/EP2018/076818 filed Oct. 2, 2018, and claims priority to European Patent Application No. 17306313.2 filed Oct. 2, 2017, the disclosures of which are hereby incorporated by reference in their entirety.

BACKGROUND OF THE INVENTION

Fiend of the Invention

The present invention relates to a packaging device for containing a plurality of medical containers and a method for removing the plurality of medical containers from this packaging device.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a container contained in the packaging device of the invention, and the "proximal direction" is to be understood as meaning the opposite direction to said direction of injection, that is to say the direction towards the user's hand holding a container as for an injection operation.

Description of Related Art

Medical containers, such as pre-fillable or prefilled syringes, often need to be transported from one site to another site, for instance from a manufacturing site to a second site where the medical containers may be filled with an agent, such as a vaccine, a medicine or a therapeutic agent. Less frequently, the medical containers may be manufactured and filled in the same first site and then be transported to a storage site. During transportation, the medical containers are usually put into a global packaging, this global packaging comprising a nest supporting the medical containers, a housing or tub containing the nest, a sealing cover closing the tub, and a so-called header bag ensuring sterility.

The nest is a plate-shaped tray that is generally configured to support more than one hundred medical containers. The nest is placed inside the box-shaped tub or housing which has one opening sealed by the sealing cover. The box-shaped housing or tub provides a simple and efficient storage and transportation solution for a plurality of medical containers. Removal of the nest holding the medical containers from the tub just requires removal of the sealing cover and extraction of the plate-shaped nest from the tub by translating this nest through the opening of the tub. This process has the advantage of being simple and thus requires limited equipment.

Document EP0439740 discloses a packaging for a plurality of disposable medical devices, such as syringes and catheters.

There is however a constant need to limit the storage or transportation costs. Besides, there is a need not to complicate the removal of the medical containers.

SUMMARY OF THE INVENTION

An aspect of the invention is a packaging device configured to contain a plurality of medical containers, said packaging device allowing storage and transportation costs reduction.

An aspect of the invention is a packaging device configured to support medical containers, the packaging device comprising a first set of supporting units configured to support a first plurality of medical containers and a second set of supporting units configured to support a second plurality of medical containers, the first set of supporting units and the second set of supporting units being configured to support said first plurality of medical containers and said second plurality of medical containers so that the first plurality of medical containers and the second plurality of medical containers are supported in an inverted position relative to each other.

The packaging device of the invention therefore enables to reduce storage and transportation costs.

Advantageously, the supporting units of the first set of supporting units are contained in a first plane, the supporting units of the second set of supporting units being contained in a second plane, the second plane being parallel to the first plane.

Advantageously, the first plane and the second plane are spaced so that at least one medical container supported by the first set of supporting units is inserted at least partially between adjacent medical containers supported by the second set of supporting units. This configuration enables to store more medical containers in a smaller volume.

Advantageously, the supporting units are configured so that the medical containers supported by the first set of supporting units are stored in a head-to-tail configuration with respect to the medical containers supported by the second set of supporting units. The packaging device of the invention thus contains about twice more medical containers than a conventional packaging device, without doubling its size. In other words, the packaging device according to the invention contains twice more medical containers per volume unit than a conventional packaging device.

Moreover, removal of the medical containers remains simple and does not need high investment costs so as to adapt the equipment used for handling a traditional packaging device. Indeed, the second plurality of medical containers can be extracted exactly the same way as the first plurality of medical containers after the packaging device has been turned over.

The packaging device is configured to maintain the first and second pluralities of medical containers in an inverted position. Therefore, the packaging device preferably comprises first and second maintaining elements configured to respectively maintain the first and second pluralities of medical containers relative to the first and second sets of supporting units. Preferably, at least one of these maintaining elements is a sealing element such as a sealing film which may be peeled off so as to access one of the first or second plurality of medical containers, as described hereinafter in further detail. The other maintain element may be either a sealing element too, or a bottom wall of a housing of the packaging device.

The packaging device according to any of the previous aspect may also comprise one or several of the following technical features, taken individually or according to all possible technical combination.

The supporting units of said first set of supporting units and the supporting units of said second set of supporting units may advantageously be offset relative to each other.

In other words, the supporting units of the first set of supporting units do not face, are not aligned with the supporting units of said second set of supporting units with respect to the longitudinal axis A. This enables to store the medical containers in a lower volume.

Advantageously, the supporting units of said first set of supporting units and the supporting units of said second set of supporting units are arranged in staggered rows relative to each other.

Having medical containers of the first plurality of medical containers which are in quincunx with respect to the medical containers of the second plurality of medical containers enables to reduce the volume of the packaging device, and therefore to limit the storage and transportation costs.

In embodiments, the supporting units of said first set of supporting units delimit first apertures, each of said first apertures being configured to receive one medical container of said first plurality of medical containers, and the supporting units of said second set of supporting units delimit second apertures, each of said second apertures being configured to receive one medical container of said second plurality of medical containers, and said first apertures being arranged in staggered rows relative to said second apertures.

In embodiments, the supporting units of said first set of supporting unit comprise first axial stops, each of the first axial stops being configured to support a flange of a medical container of said first plurality of medical containers, and the supporting units of said second set of supporting units comprise second axial stops oriented opposite to the first axial stops, each of the second axial stop being configured to support a flange of a medical container of said second plurality of medical containers.

The first and second axial stops may be spaced from each other so that a distal end of a medical container of the first, respectively second, plurality of medical containers is located between medical containers of the second, respectively the first, plurality of medical containers. This helps to increase the number of medical containers per volume unit.

In embodiments, the supporting units of said first and second sets of supporting units are configured so that said first plurality of medical containers is removable from the packaging device along a first direction with respect to the longitudinal axis A, and the second plurality of medical containers is removable along a second direction opposite said first direction.

For example, the supporting units of the first set of supporting units have the first aperture which allows removal of the first plurality along said first direction and the supporting units of the second set of supporting units have the second aperture which allows removal of the second plurality of medical containers in said second direction.

For example, each supporting unit may have an axial stop onto which is configured to abut a corresponding medical container. The axial stops of the first and second sets of supporting units are preferably oriented opposite to each other, so that axial stops of the first set of supporting units are configured to stop an axial movement of the first plurality of medical containers along the second direction whereas axial stops of the second set of supporting units are configured to stop an axial movement of the second plurality of medical containers along the first direction.

The packaging device may comprise at least one opening configured to allow removal of the first plurality of medical containers from the first set of supporting units along said first direction.

The packaging device may also comprise a second opening opposite said at least one opening with respect to a longitudinal axis A, said second opening being configured to allow removal of the second plurality of medical containers from the second set of supporting units along said second direction.

In embodiments, the packaging device comprises two nests: a first nest including the first set of supporting units and a second nest including the second set of supporting units.

Having two distinct nests provides a possibility to handle the first and second pluralities of medical containers separately. The nests may be plate-shaped.

In an embodiment, the packaging device comprises:
a housing delimiting an internal volume, the two nests being located inside the housing, and
at least one opening leading into the internal volume, said at least one opening being configured to allow insertion or removal of at least one of the two nests inside or outside the housing.

The first nest and the second nest may be arranged in an inverted position relative to each other.

In embodiments, the second opening leads into the internal volume, said second opening being configured to allow insertion or removal of the second of the two nests inside or outside the housing.

As a result, removal of both nests outside the housing remains simple, as it only requires an extra rotation-step of the packaging device. Indeed, after having removed the first nest as usual, only one extra step is thus needed in order to rotate the packaging device and the second nest can be removed in the same way as it was done for the first nest.

The housing may thus preferably have two openings comprising the at least one opening and a second opening, said openings being configured to allow insertion or removal of respectively the first nest and the second nest.

Advantageously, the packaging device comprises two opposite abutment surfaces protruding from an inner side of the housing, the nests being configured to rest on said abutment surfaces.

The nests are just put down on the corresponding abutment surface, without further attachment. This provides easier placement and removal of the nests.

The two opposite abutment surfaces each faces one of the two openings.

In embodiments, the supporting units are configured to support an end of the medical containers and the packaging device comprises a lateral guiding surface configured to prevent a lateral movement of an opposite end of the medical containers with respect to a longitudinal axis A.

Each of the medical containers may therefore be supported by both sets of supporting units, more precisely by both nests, which limits the risks of impacts between adjacent medical containers, while limiting the volume occupied by the medical containers, and therefore limiting the volume of the packaging device. The lateral guiding surface may be configured to extend at a distal end of the medical containers. The supporting units may be configured to support a proximal end of the medical containers.

In embodiments, the packaging device comprises at least one sealing element configured to close the packaging device in order to keep sterility of a volume configured to contain the medical containers.

Said at least one sealing element may close the at least one opening. Therefore, the at least one sealing element allows keeping the internal volume sterilized.

In embodiments, the at least one sealing element is permeable to a sterilization gas.

This enables easy sterilization process.

In embodiments, the packaging device comprises a second sealing element configured to close the packaging device in order to keep sterility of the volume configured to contain the medical containers, and at least one of the two sealing elements is permeable to a sterilization gas.

The second sealing element may be configured to close the second opening. Therefore, the second sealing element allows keeping the internal volume sterilized.

In embodiments, the two sealing elements are permeable to a sterilization gas.

This embodiment enables to create a circulation conduit for a sterilization gas when the packaging devices are stacked on one another. The sterilization gas can circulate from a packaging device to another through the aligned sealing elements.

In embodiments, the packaging device comprises two sealing elements configured to close the packaging device in order to keep sterility of a volume configured to contain the medical containers, one of said two sealing elements having an internal face configured to maintain said first plurality of medical containers in the first set of supporting units and the other of said two sealing elements having an internal face configured to maintain said second plurality of medical containers in the second set of supporting units.

This allows reliable maintaining and easy removal of the medical containers. As soon as the sealing elements are peeled off, it is possible to remove the medical containers.

In embodiments, the supporting units comprise a guiding conduit.

This limits the movements of the medical containers relative to the supporting units, more precisely the nest to a translational movement such as an axial movement. The medical containers are therefore supported in a more stable way.

In embodiments, the packaging device comprises two opposite bearing surfaces.

This enables to stack several packaging devices onto each other and possibly to seal the openings. The bearing surfaces may be provided at opposite ends of a lateral wall of the housing. The bearing surfaces may extend around the openings.

In embodiments, the packaging device comprises a side wall configured to lean against a supporting surface so as to permit the packaging device to lie in a side rest position.

Therefore, during storage, the packaging device may be positioned on the edge, so that the medical containers are stored horizontally. This prevents silicone migration inside the medical containers. Indeed, the inner wall of the medical containers may be coated with silicone in order to ease gliding of a stopper. However, during storage, the silicone may migrate towards a tip of the medical container, which might block up the container tip channel or the needle channel when there is one attached to the tip of the container.

Another aspect of the invention is a method for sterilizing several packaging devices having two openings as above described, comprising the steps of:
  stacking up the packaging devices so that the openings of the stacked packaging devices are aligned,
  circulating a sterilization gas through the stack of packaging devices.

This permits a more efficient and faster sterilization process.

Another aspect of the invention is a method for removing the pluralities of medical containers from a packaging device as above described, comprising the steps of:
  removing the first plurality of medical containers supported by the first set of supporting units outside the packaging device,
  turning the packaging device over,
  removing the second plurality of medical containers supported by the second set of supporting units.

More precisely, the method may comprise the steps of:
  removing the first plurality of medical containers supported by the first nest outside the housing of the packaging device through the at least one opening,
  turning the second nest over,
  removing the second plurality of medical containers supported by the second nest.

In embodiments, the step of turning the second nest over comprises turning the housing containing the second nest over, that is to say turning the housing and the second nest together. Alternatively, the step of turning the second nest may comprise turning the second nest alone, without turning the housing.

The step of removing the first plurality of medical containers may comprise removing the first nest supporting said first plurality of medical containers outside the housing through the at least one opening, for example by means of a translational movement.

The step of removing the first plurality of medical containers may only comprise removing of the medical containers of said first plurality of medical containers without removing the first nest outside the housing. The empty first nest may then be removed from the housing during a further step.

The step of removing the second plurality of medical containers may comprise removing the second nest supporting said second plurality of medical containers outside the housing, for example by means of a translational movement.

Removal of the second nest outside the housing may be performed by means of a movement of either the housing or the second nest with respect to each other.

The step of removing the second plurality of medical containers may only comprise removing of the medical containers of said second plurality of medical containers without removing the second nest outside the housing. The empty second nest may then be removed from the housing during a further step.

In embodiments, the packaging device comprises at least one sealing element and the method comprises the step of removing the at least one sealing element so as to open said at least one opening before removing the first plurality of medical containers.

In embodiments, the packaging device comprises a second opening and a second sealing element closing said second opening, and the method comprises a step of removing the second sealing element so as to open the second opening after rotation of the second nest or of the housing, and removing the second plurality of medical containers outside the housing through said second opening.

The step of removing the second plurality of medical containers may comprise removing of said second plurality of medical containers through the at least one opening, more precisely through the same opening as the first plurality of medical containers.

The step of removing the second plurality of medical containers may comprise removing of said second plurality of medical containers through the second opening, more precisely through the other of the two openings, that is to say the other than the one used for removal of the first plurality of medical containers.

BRIEF DESCRIPTION OF THE DRAWINGS

The invention and the advantages arising therefrom will clearly emerge from the detailed description that is given below with reference to the appended drawings as follows:

FIGS. 9A and 9B are cross section views of a packaging device according to an embodiment of the invention.

DESCRIPTION OF THE INVENTION

Figure 1:
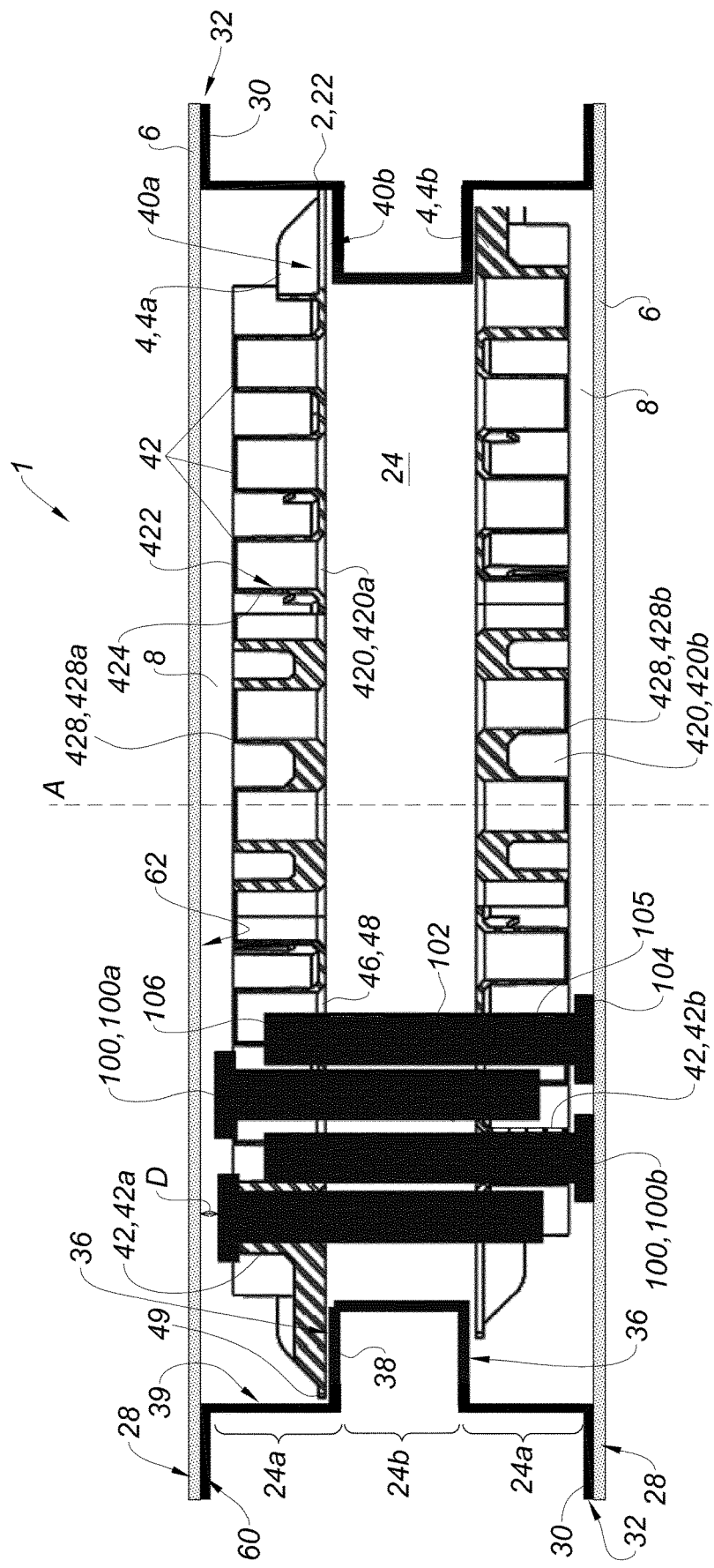
FIG. 1 is a diagrammatic view of a packaging device according to an embodiment of the invention.

With reference to FIG. 1 is shown a packaging device 1 of the invention. The packaging device 1 of the invention is intended to contain a plurality of medical containers 100. The medical containers 100 may be vials or preferably syringes, such as pre-fillable or prefilled syringes. The medical containers 100 are intended, after filling, to contain a medical agent such as a vaccine, a medicine or a therapeutic agent.

The medical containers 100 typically comprise an elongated barrel 102 defining a reservoir for containing said vaccine, medicine or therapeutic agent. The tube-shaped barrel 102 may be cylindrical. The medical container 100 includes a flange 104 at a proximal end 105 of the barrel 102, and a tip closed by a needle and/or a cap 107 at a distal end 106 of the medical container 100.

The packaging device 1 comprises supporting means which are configured to support the medical containers 100. The medical containers 100 contained inside the packaging device 1 may be arranged parallel to each other and to a longitudinal axis A.

With reference to FIG. 1, the supporting means comprise a first set of supporting units 42a which are configured to support a first plurality of medical containers 100a, and a second set of supporting units 42b which are configured to support a second plurality of medical containers 100b.

The first supporting units 42a and the second supporting units 42b are arranged relative to each other so that the medical containers 100a of said first plurality of medical containers 100 and the medical containers 100b of said second plurality of medical containers 100 are supported in an inverted position, that is to say oriented in opposite directions with regard to axis A, as can be seen for example on FIGS. 1, 2A, 9A, 9B, 10 and 11.

The first set of supporting units 42a may preferably be configured to support the medical containers 100a of said first plurality of medical containers in a first horizontal plane which is orthogonal to said longitudinal axis A. Likewise, the second set of supporting units 42b may be configured to support the medical containers 100b of said second plurality of medical containers in a second horizontal plane which is orthogonal to said longitudinal axis A and which is away from the first horizontal plane.

The first plane and the second plane may be spaced from each other so that at least one medical container 100a supported by the first set of supporting units 42a is inserted at least partially between at least two medical containers 100b, and preferably four medical containers 100b, supported by the second set of supporting units 42b.

The supporting units 42 are preferably configured so that the medical containers 100a supported by the first set of supporting units 42a are stored in a head-to-tail configuration with respect to the medical containers 100b supported by the second set of supporting units 42b. By first and second medical containers 100a, 100b stored in a head-to-tail configuration it is meant that the distal end 106 of one first medical container 100a is located between a proximal end 105 and the distal end 106 of the at least two, preferably four, adjacent medical containers 100b which are positioned around. Preferably, the distal end 106 of one first medical container 100a is located closer to the proximal end 105 than the distal end 106 of one second medical container 100b.

The first set of supporting units 42a may be configured to support the first plurality of medical containers 100a so that the medical containers 100a of the first plurality of medical containers 100a are arranged in parallel rows. The second set of supporting units 42b may be configured to support the second plurality of medical containers 100b so that the medical containers 100b of the second plurality of medical containers 100b are arranged in parallel rows. Besides, the first and second sets of supporting units 42a, 42b may be arranged relative to each other so that the packaging device 1 comprises alternate rows of medical containers of the first plurality of medical containers 100a and medical containers of the second plurality of medical containers 100b.

The supporting units of said first set of supporting units 42a and the supporting units of said second set of supporting units 42b are preferably arranged in staggered rows relative to each other. By supporting units 42 of the first and second sets arranged in staggered rows relative to each other, it is meant that between four adjacent supporting units 42 of one of the first or second set of supporting units is delimited an area which faces one supporting unit 42 of the other of the first or second set of supporting units, having regard to the longitudinal axis A.

As shown on the figures, the first set of supporting units 42a and the second set of supporting units 42b are configured to support the flange 104 of the medical containers 100a, 100b, as will be described hereinafter in further details. The flanges 104 thus lean against the corresponding supporting units 42a, 42b.

For example, the first and second sets of supporting units 42a, 42b respectively comprise first and second axial stops 428a, 428b. These axial stops 428 are configured to support the flange 104 of one medical container 100. The first and second axial stops 428a, 428b are preferably oriented opposite to each other. The first and second axial stops 428a, 428b may be spaced from each other so that a distal end 106 of a medical container 100a, 100b does not extend beyond the proximal end 105 of the adjacent medical containers 100*b*, 100*a*. Therefore, the first and second axial stops 428*a*, 428*b* may be configured so that a distal end 106 of a medical container 100*a*, 100*b* is at a level comprised between a proximal end 105 and the distal end 106 of a medical container 100*b*, 100*a* of the other plurality of medical containers 100.

The supporting units of the first and second sets of supporting units 42*a* preferably delimit first and second apertures 420*a*, 420*b*. Each of said first and second apertures 420*a*, 420*b* is configured to receive one medical container 100*a*, 100*b*.

The supporting units 42 may comprise a guiding conduit 424 in order to allow a translational movement along axis A of the medical containers 100 relative to the supporting units 42.

It should be noted that the supporting units 42*a*, 42*b* are preferably configured to support the proximal end 105 of the medical containers 100, while the packaging device 1 may further comprise lateral guiding surfaces 46 configured to prevent a lateral movement of the distal end 106 of the medical containers 100 with respect to a longitudinal axis A, so as to prevent collisions between adjacent medical containers 100*a*, 100*b* during transportation.

In order to prevent the medical containers 100 from inadvertently leaving the supporting units 42, the packaging device 1 preferably comprise a retaining element, such as an internal face 62 of a sealing element 6.

According to an embodiment shown on FIG. 1, the packaging device 1 may comprise a housing 2, two nests 4 positioned inside the housing 2, and at least one opening 8 leading into the housing and providing a passage for inserting or removing the nests 4 into or outside the housing 2. A nest is a plate provided with apertures, hereinafter apertures 420, aligned according to predetermined rows, each hole being configured to receive the barrel of one medical container. The packaging device 1 may also comprise at least one sealing element 6 for sterilizingly closing the at least one opening 8. Preferably, the packaging device 1 comprises two opposite openings 8 and two sealing elements 6.

The first set of supporting units 42*a* may be arranged on a first nest 4*a*, whereas the second set of supporting units 42*b* may be arranged on a second nest 4*b*.

The housing 2 comprises a lateral wall 2 which may extend around a preferably straight longitudinal axis A. The housing 2 may have four side walls 22 so that the housing 2 may have a rectangular or square shape. The housing 2 defines an internal storage volume 24.

The internal volume 24 may be divided into several portions, for example three portions: two accommodation portions 24*a* each intended to receive a nest 4, and a central portion 24*b* extending between said two accommodation portions 24*a*.

The at least one or the two openings 8 lead into said internal volume 24. More precisely, each opening 8 may lead into one of the accommodation portions 24*a*. The openings 8 may be delimited by opposite ends of the housing 2, so that the at least one and the second openings 8 are opposite with respect to the axis A. As shown on FIG. 1, the openings 8 are axial openings, through which goes the longitudinal axis A. The openings 8 are preferably coaxial. The openings 8 may be similar in shape and dimensions. The openings 8 preferably extend perpendicular to the longitudinal axis A, and therefore are preferably parallel to each other. The one or two openings 8 are configured to allow passage of the nests 4 through these openings 8, for example by means of a translational movement of said nests 4 along the longitudinal axis A. Each opening 8 may therefore face one of the two nests 4. The openings 8 and the nests 4 may have a complementary shape. The openings 8 preferably have dimensions greater than that of the nests 4.

The two nests 4 are positioned inside the internal volume 24. More precisely, the two nests 4 may be positioned inside the accommodation portions 24*a*. The nests 4 may have a rectangular or square plate shape, so as to correspond to the shape of the housing 2. The nests 4 may comprise two opposite faces 40*a*, 40*b*, such as a first face 40*a* for supporting medical containers 100, and a second face 40*b* for positioning the nests 4 inside the internal volume 24. The nests 4 are preferably positioned perpendicular to the longitudinal axis A, or parallel to each other. As visible on FIG. 1, the nests 4 are arranged in an inverted position relative to each other, that is to say that the second faces 40*b* of the two nests 4 face each other. The head to tail configuration of the two nests 4 enables the medical containers 100 supported by one of these two nests 4 to extend adjacent to the medical containers 100 supported by the other of these two nests 4, that is to say side by side, thereby reducing height of the packaging device 1. The medical containers 100 of both nests 4 may extend side by side in a zone corresponding to the central portion 24*b* of the internal volume 24.

The first nest 4*a* and the second nest 4*b* may be similar. Each nest 4*a*, 4*b* comprises a set of supporting units 42 so that the first and second nests 4*a*, 4*b* are configured to support respectively a first plurality of medical containers 100*a* and a second plurality of medical containers 100*b*. For example, each nest 4 may support 100 or 160 medical containers 100. As shown on FIGS. 1 to 11, the first nest 4*a* and the second nest 4*b* are distinct from each other and are removable from the housing 2.

Each supporting unit 42 may be configured to support a proximal end 105 of one medical container 100. The first set of supporting units 42*a* and the second set of supporting units 42*b* may be arranged relative to each other in staggered rows, in quincunx, so that the medical containers 100*a* of the first plurality of medical containers 100 may extend between adjacent medical containers 100*b* of the second plurality of medical containers 100 and conversely, the medical containers 100*b* of the second plurality of medical containers 100 may extend between adjacent medical containers 100*a* of the first plurality of medical containers 100 in the same central portion 24*b*.

By medical containers 100*a*, 100*b* arranged in staggered rows or quincunx relative to each other, it is meant that between four adjacent medical containers 100*a* of the first plurality of medical containers 100 extends a medical container 100*b* of the second plurality of medical containers 100, and conversely between four adjacent medical containers 100*b* of the second plurality of medical containers 100 extends a medical container 100*a* of the first plurality of medical containers 100.

The supporting units 42 of the first or second set of supporting units are preferably arranged according to a predetermined pattern. For example, the supporting units 42 may be aligned so as to form a grid pattern of perpendicular rows, as visible for instance on FIGS. 10 and 11. Alternatively, the supporting units 42 may be arranged in staggered rows.

Preferably, the supporting units 42 of both first and second sets of supporting units are similar to each other.

The supporting units 42 may be arranged on the first face 40*a* of the nests 4. The supporting units 42 may comprise an aperture 420, such as a through-hole, which may be configured to permit insertion or removal of a medical container 100 through the corresponding nest 4. The apertures 420 and the barrel 102 of the medical containers 100 preferably have a complementary shape. The supporting units 42 could only comprise the apertures 420.

The apertures 420 of the first set of supporting units 42a may be arranged so as to allow removal of the first plurality of medical containers 102a along a first direction of the longitudinal axis A, whereas the apertures 420 of the second set of supporting units 42b may be arranged so as to allow removal of the second plurality of medical containers 102b along a second direction of the longitudinal axis A opposite the first direction.

The supporting units 42 may preferably comprise at least one lateral guiding surface 422 configured to delimit a guiding conduit or tube 424, such as a tubular sleeve, for receiving and guiding a medical container 100. The guiding conduits 424 may be parallel to each other and may extend along the longitudinal axis A. Each guiding conduit 424 leads into the reception aperture 420. The guiding conduits 424 may protrude from the first face 40a of the nest 4. The guiding surfaces 422 and/or guiding conduits 424, and the barrel 102 of the medical container 100, may also have a complementary shape.

The supporting unit 42 may include an axial stop 428, which may be delimited by an end of the guiding conduit 424, said axial stop 428 being configured to stop insertion of a medical container 100 into the reception aperture 420. More precisely, the flange 104 of the medical containers 100 may be designed to abut on said axial stop 428. In particular, the outer diameter of the flange 104 of the medical containers 100 is greater than the diameter of the guiding conduit 424 or reception aperture 420. The axial stops 428 of the first and second sets of supporting units 42a, 42b are preferably directed in opposite directions.

The packaging device 1, for example the nests 4, may advantageously comprise guiding means configured to guide the medical containers 100 with regard to the longitudinal axis A. The guiding means arranged on one of the two nests 4 may thus prevent or at least limit a lateral movement of the medical containers 100 which are supported by the other nest 4. As a result, the guiding means of the first nest 4a are configured to immobilize the second plurality of medical containers 100, while the guiding means of the second nest are configured to immobilize the distal end 106 of the first plurality of medical containers 100. The guiding means are configured to at least radially maintain the containers 100, in order to prevent radial movements of the containers 100 during handling of the packaging device 1.

With reference to FIGS. 9A and 9B, the guiding means are configured to maintain a distal end 106 of the containers 100. More precisely, the guiding means may be configured to maintain a distal end 106 of the barrel 102. For example, the guiding means are configured to maintain any device mounted on said distal tip such as for example a closure cap 107.

The guiding means of the first nest 4a may be similar to the guiding means of the second nest 4b.

The guiding means comprise a plurality of guiding units 45, each guiding unit 45 being configured to maintain a distal end 106 of one medical container 100. A first set of guiding units 45a may be configured to maintain an end of the medical containers 100b supported by the second set of guiding units 42b, whereas a second set of guiding units 45b may be configured to maintain an end of the medical containers 100a supported by the first set of guiding units 42a. The guiding units 45 of both nests 4 may be similar to each other. The guiding units 45 may be arranged on the second face 40b of the nests 4. The guiding units 45 and the supporting units 42 of a same nest 4 or set are preferably arranged in staggered rows, that is to say that the guiding units 45 extend between adjacent supporting units 42. It should also be noted that the guiding units 45a of the first nest 4a may face the supporting units 42b of the second nest 4b having regard to the longitudinal axis A. Similarly, the guiding units 45b of the second nest 4b may face the supporting units 42a of the first nest 4a having regard to the longitudinal axis A. In other words, the guiding units 45 of the first or second nest 4a, 4b may be aligned with the supporting units 42 of respectively the second or first nest 4b, 4a with respect to longitudinal axis A.

The guiding units 45 may comprise an aperture 48, such as a through-hole. The guiding units 45 or the aperture 48 may comprise a lateral guiding surface 46 configured to stop a radial movement of a medical container 100. The guiding surface 46 may be delimited by said aperture 48. The distal ends 106 or barrels 102 of the medical containers 100 and the guiding surface 46 or aperture 48 may have a complementary shape. This guiding surface 46 or aperture 48 may be arranged on the second face 40b of the nests. As a result, each medical container 100 is maintained by both nests 4. This prevents radial movement of the medical containers 100 during transportation. The medical containers 100 therefore remain parallel to each other, and preferably to the longitudinal axis A. Impacts between adjacent medical containers 100 are thus avoided.

The two removable sealing elements 6 are configured to close the openings 8 so that the internal volume 24 delimited by the housing 2 and these two sealing elements 6 is maintained sterile. The sealing elements 6 may therefore comprise a microbial barrier. The sealing elements 6 may also be permeable to a sterilization gas, so that the interior of the packaging device 1 can be sterilized while the sealing elements 6 close the two openings 8. The sterilization gas may be for instance ethylene oxide (EO). In one embodiment, one of the sealing elements 6 may comprise a Tyvek® sheet or any material that is airtight but permeable to a sterilization gas such as for example ethylene oxide, and the other sealing element 6 may comprise a different material, for example a plastic material such as a polyethylene (PE) sheet. In another embodiment, the two sealing elements 6 may comprise a Tyvek® sheet so as to permit a sterilization gas to flow through the packaging device 1, or through a stack of packaging devices 1 where the sealing elements 6 of adjacent packaging devices 1 are in contact with each other.

The packaging device 1 may comprise a sealing bag (not shown) completely enclosing the housing 2. The sealing is configured to keep the internal volume 24 sterilized. This sealing bag may form the at least one sealing element. This sealing bag, or header bag, may comprise a material which is permeable to a sterilization gas, such as Tyvek®. The sealing bag may also be a plastic bag or a combination of both materials, plastic and permeable to gas sterilization.

The sealing elements 6 are configured to be removed before removing the nests 4. The sealing elements 6 may comprise an attachment surface 60 configured to be attached to the housing 2. The attachment surface 60 of the sealing members 6 may extend all along a peripheral rim of the sealing members 6. Preferably, the attachment surface 60 of the sealing member is glued, for example thermo glued, on the housing 2.

The packaging device 1 advantageously comprises opposite bearing surfaces 28 so as to permit stacking of several packaging devices 1. The bearing surfaces 28 may be located at opposite ends of the housing 2. The opposite bearing surfaces 28 are preferably perpendicular to the longitudinal axis A, and may be parallel to each other. The opposite bearing surfaces 28 may extend around each of the openings 8. The opposite bearing surfaces 28 may be delimited by a flange 30 extending from an end of the housing 2. It should be noted that the sealing elements 6 may be attached to these bearing surfaces 28.

The packaging device 1 may also comprise at least a side wall 22 configured to permit the packaging device 1 to lie in a side rest position. This side wall may include a side bearing surface 32, which may be parallel to the longitudinal axis A, and to the guiding conduits 424 and/or the medical containers 100 so that the packaging device 1 may rest on a side. The packaging device 1 preferably includes two opposite side bearing surfaces 32. In the example shown on FIG. 1, the side bearing surfaces 32 are delimited by an edge of the flanges 30.

The packaging device 1 may comprise two opposite axial abutment surfaces 36 extending inside the internal volume 24 so as to support the nests 4. The axial abutment surfaces 36 may protrude from an inner side of the housing 2. Alternatively or complementarily, the axial abutment surfaces 36 may be delimited at opposite ends of a spacer, for example a spacer bar, which is interposed between the nests 4 so as to maintain at a predetermined distance. The abutment surfaces 36 are configured to stop insertion of the nests 4 inside the internal volume 24. The abutment surfaces 36 preferably extend perpendicular to the longitudinal axis A and preferably face a corresponding opening 8. Preferably, the second face 40b of the nests 4 just rests on the corresponding abutment surface 36, without further attachment.

The abutment surfaces 36 may be delimited by corresponding shoulders 38 extending inside the internal volume 24. Alternatively or complementarily, the abutment surfaces 36 may be delimited by ribs or protrusions arranged on an inner side of the housing 2.

It should be noted that the housing 2 may be devoid of such abutment surfaces 36 or shoulders 38, and may comprise other spacing means in order to keep the nests 4 separated at a predetermined distance from each other, such as a spacer element (not shown) which is interposed between the first nest 4a and the second nest 4b.

In order to prevent excessive movements of the medical containers 100 and of the nests 4 inside the housing 2 during handling of the packaging device 1, the sealing elements 6 presents an internal face 62 which may configured to hold back the medical containers 100 inside the corresponding supporting units 42 or nests 4 and thus hold back the nests 4 inside the accommodation portions 24a. A distance D between this internal face 62 and the flange 104 or end of the medical containers 100 supported by the corresponding nest 4 may be comprised between 0 mm and 10 mm. In other words, the height of the accommodation portions 24a may be equal to the distance between the flange 104 or end of the medical containers 100 and the second face 40b plus the aforementioned distance D. The height of the accommodation portions 24a may be the distance between the abutment surfaces 36 and the extraction openings 8.

The packaging device 1 may include lateral stopping surfaces 39 configured to limit lateral movements of the nests 4 inside the internal volume 24. The lateral stopping surfaces 39 may be part of an inner side surface of the housing 2. For example, the lateral stopping surfaces 39 may correspond to a portion of the housing 2 from which the shoulders 38 extend. The lateral stopping surfaces 39 may face and block an edge 49 of the nests 4.

Figure 12:
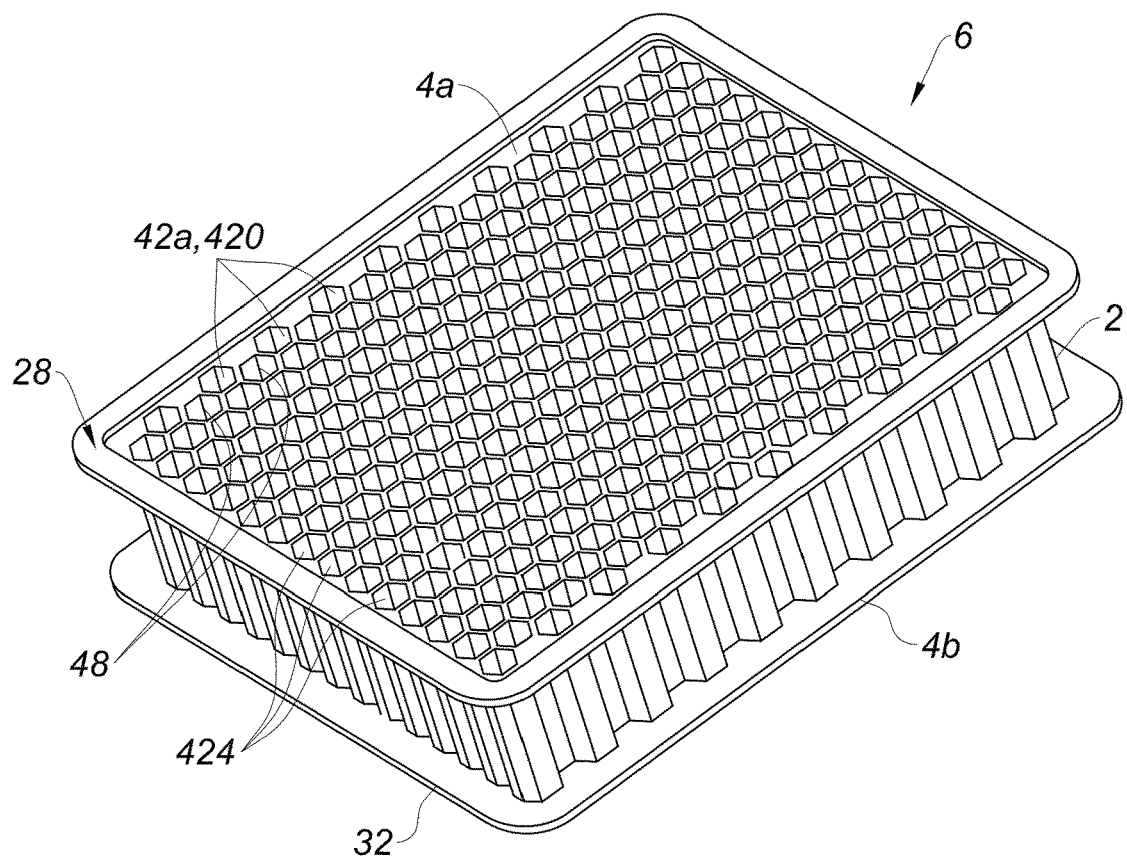
FIGS. 12, 13 and 14 are perspective views of a packaging device according to an embodiment of the invention.
Figure 13:
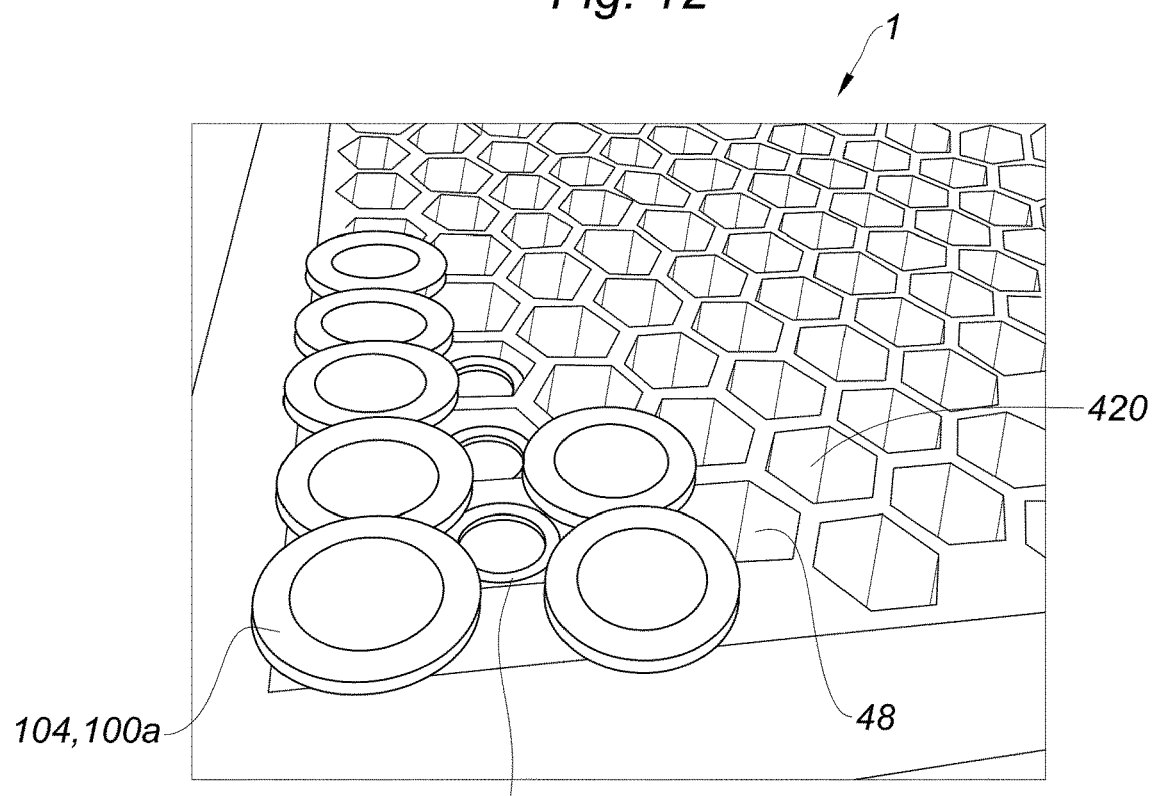
Figure 14:
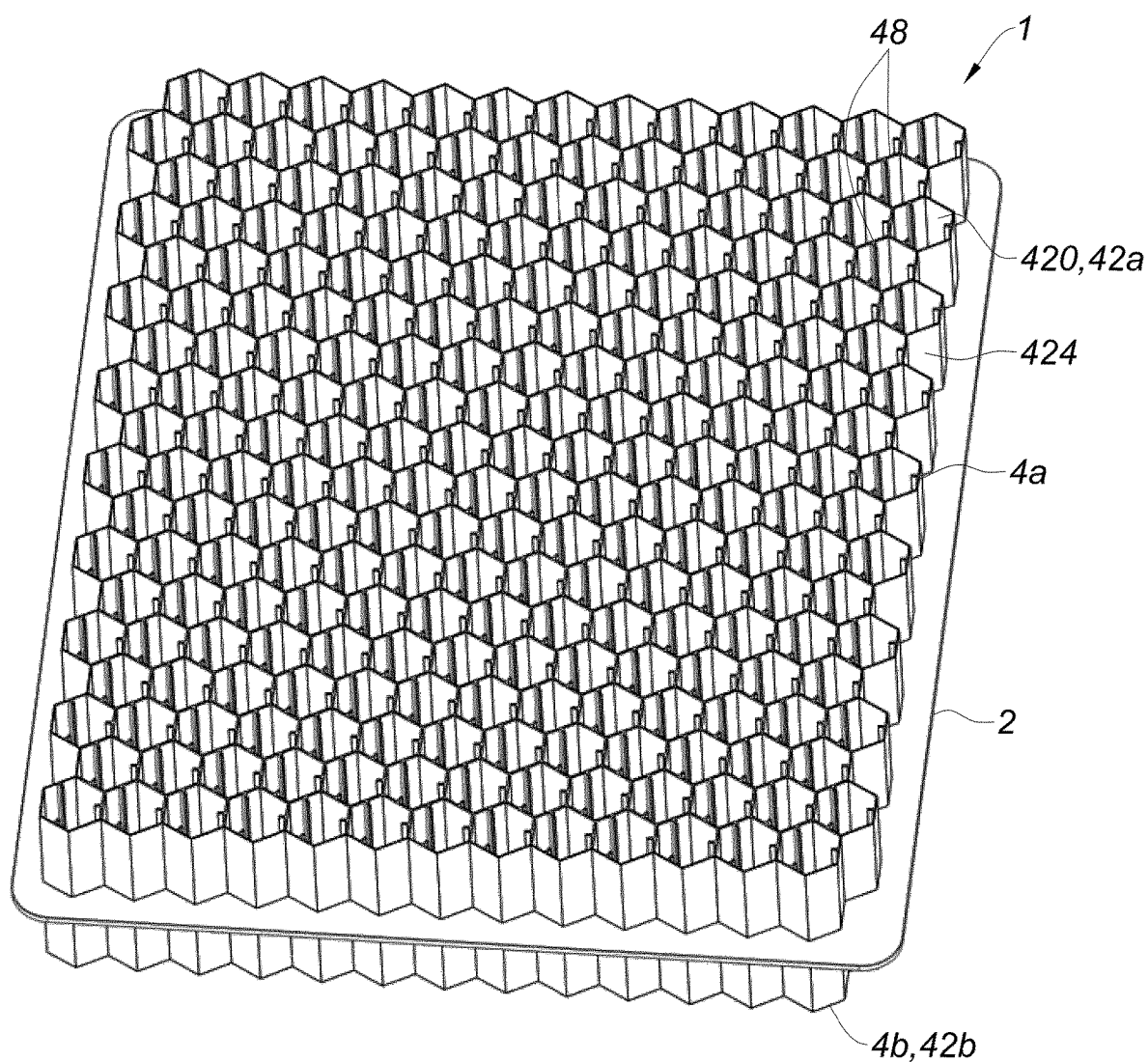

With reference to FIGS. 12 to 14 is shown a packaging device 1 according to another embodiment. The features which are similar to the above-described embodiments are designated by the same numeral references. In this embodiment, the two nests 4 and, possibly the housing 2, are molded in a single piece.

The packaging device 1 is intended to receive the medical containers 100 in a head-to-tail configuration, as shown on FIG. 14. The guiding conduits 424 are tubes provided with the aperture 420 at a first end and the aperture 48 at a second end opposite said first end. Therefore, the guiding conduits 424 connect the two nests 4. Each medical container 100 is thus maintained, from its proximal end 105 to its distal end 106, in a single compartment. The proximal end 105 of each medical container 100 is maintained by one of the two nests 4 while the distal end 106 is maintained by the other nest 4.

The guiding conduits 424 may be cylindrical or may advantageously have a polygonal cross section so as to allow a more compact storage. As shown on FIGS. 12 to 14, the guiding conduits 424 are preferably hexagonal.

It should also be noted that adjacent guiding conduits 424 share a common lateral wall portion. As a result, there is no room between adjacent guiding conduits 424. The guiding conduits 424 touch each other.

The guiding conduits 424 extend at the same height. The end of adjacent guiding conduits 424 is at the same level.

The packaging device 1 may be sealed by one or several sealing elements 6, such as Tyvek® sheet or by a sealing bag, for example under vacuum. This sealing element 6 may be configured to retain the medical containers 100 inside the guiding conduits 424.

Figure 15:
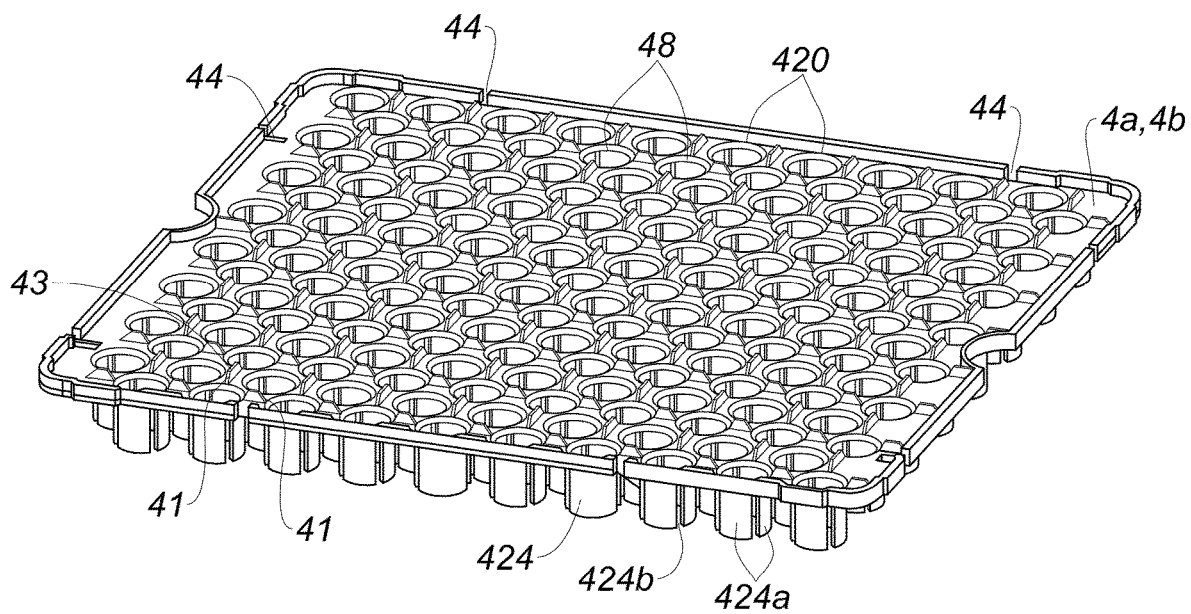
FIGS. 15 and 16 are, respectively, a perspective view and a top view of a nest of the packaging device according to an embodiment of the invention.
Figure 16:
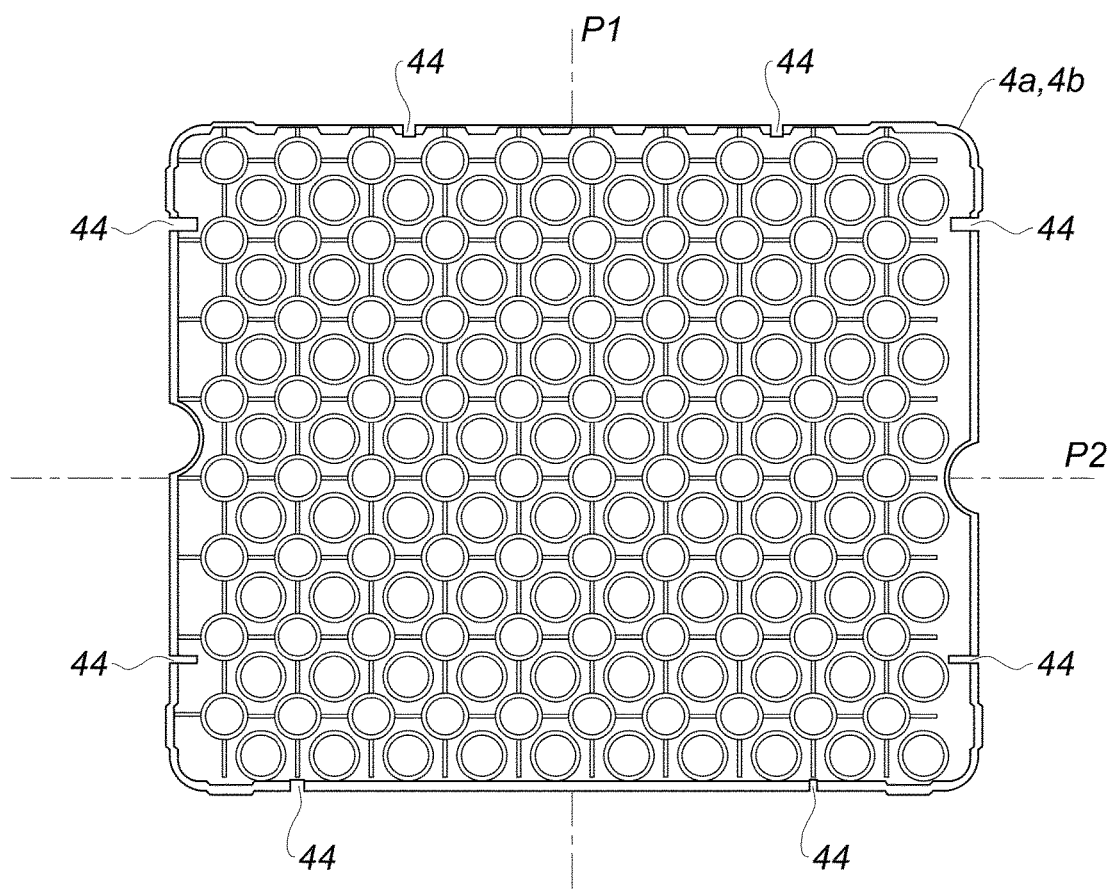

With reference to FIGS. 15 and 16 is shown a nest 4 of a packaging device 1 according to another embodiment. The features which are similar to the above-described embodiments are designated by the same numeral references.

As shown on FIGS. 15 and 16, the guiding conduits 424 may advantageously comprise at least two guiding tabs 424a, a slit 424b being delimited between said at least two guiding tabs 424a. This allows to reduce raw material costs and lighten the packaging device 1. The slits 424b extend along a direction orthogonal to the nests 4. The slits 424b preferably extend along the whole length of the guiding conduit 424.

Advantageously, the nests 4 may comprise slanted walls 41 configured to guide the distal end 106 of the medical containers 100 supported by the other nest 4 inside the apertures 48. The slanted walls 41 preferably protrude from the second face 40b of the nests 4, opposite the guiding conduits 424. The slanted walls 41 may be arranged at an end of a rib 43, so as to reduce material costs. The ribs 43 may be aligned in parallel rows so as to stiffen the nests 4. Both ends of said ribs 43 may be provided with a slanted wall 41. Besides, the ribs 43 preferably extend ortorgonal to the nests 4.

As visible on FIG. 16, the packaging device 1 may comprise keyed elements configured to allow a single predetermined positioning of the nests 4 inside the housing 2. The keyed elements may comprise slits 44 configured to engage ribs having a complementary shape. For example, one or several sides of the nests 4 are provided with the slits 44 while an internal wall of the housing 2 is provided with the complementary ribs (not shown). As visible on FIG. 16, the keyed slits 44 have different shapes or locations, so that the slits 44 are advantageously asymmetric with regard to a first vertical median plane P1 and/or to a second vertical median plane P2. The first vertical median plane P1 extends at the middle and orthogonally to longitudinal sides of the nest 4, while the second median plane P2 extends at the middle and orthogonally to transversal sides of the nest 4.

With reference to FIGS. 2A to 2F, another aspect of the invention is a method for removing the pluralities of medical containers 100 from a packaging device 1 as above described.

Figure 2A:
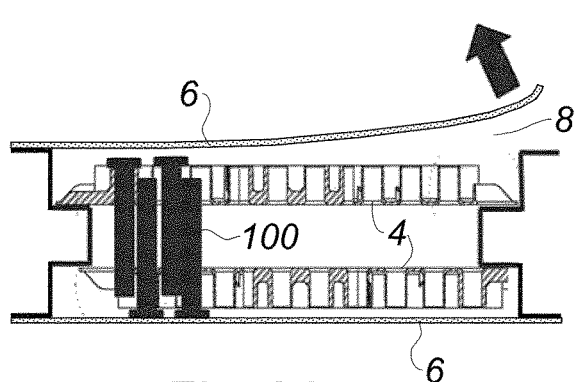
FIGS. 2A to 2F are diagrammatic views illustrating steps of a method for extracting the medical containers contained in a packaging device according to an embodiment of the invention.
Figure 2B:
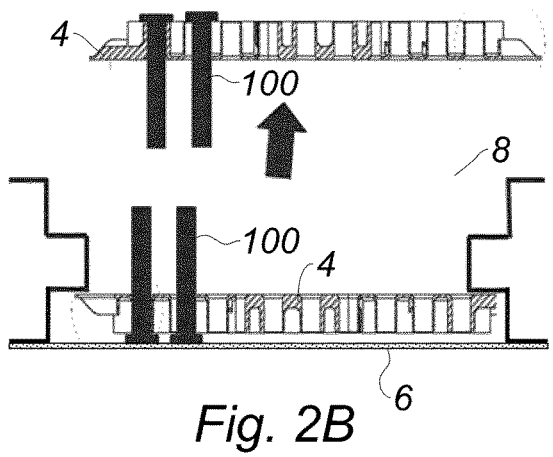
Figure 2C:
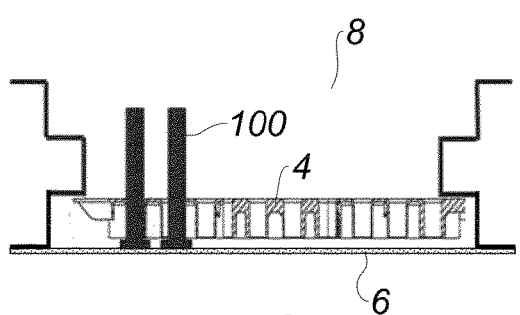
Figure 2D:
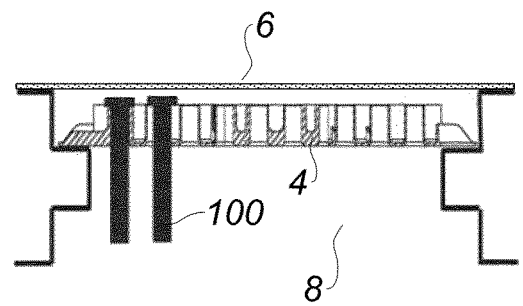
Figure 2E:
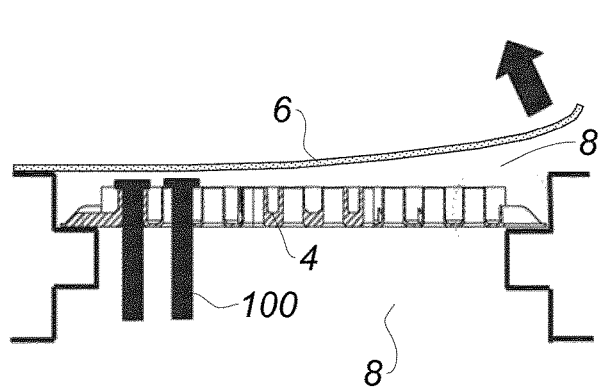
Figure 2F:
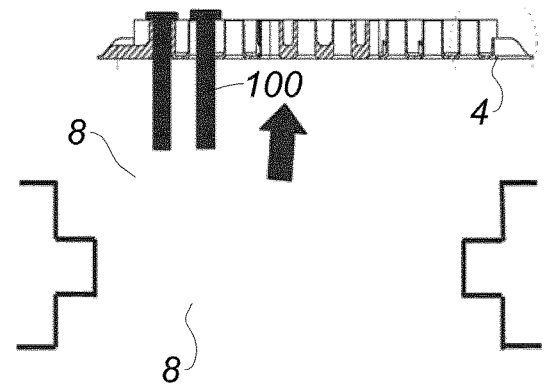
Figure 3:
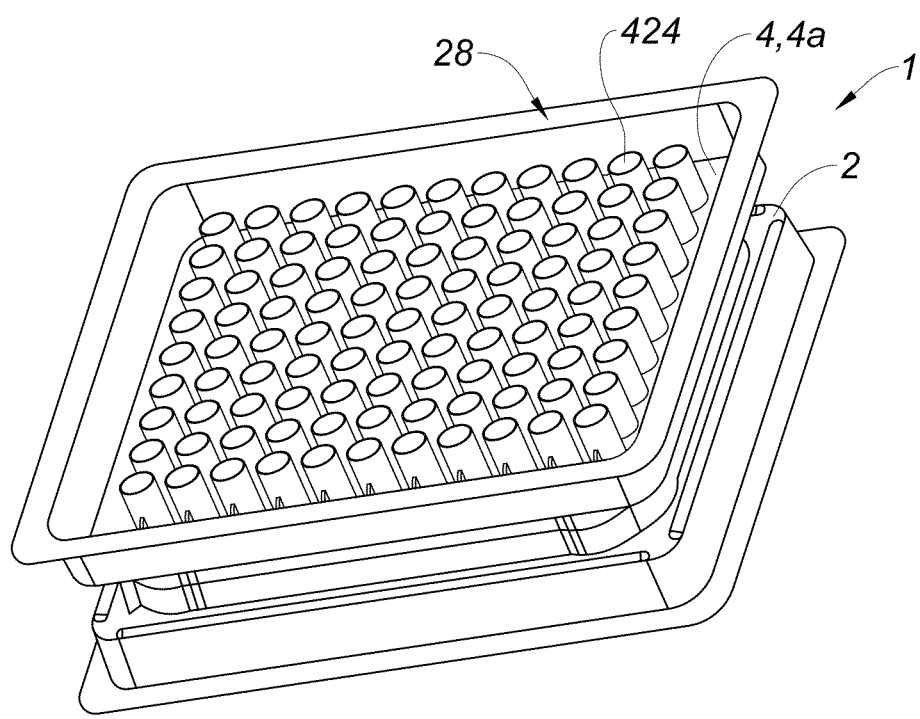
FIGS. 3 and 4 are perspective views of a packaging device according to an embodiment of the invention.
Figure 4:
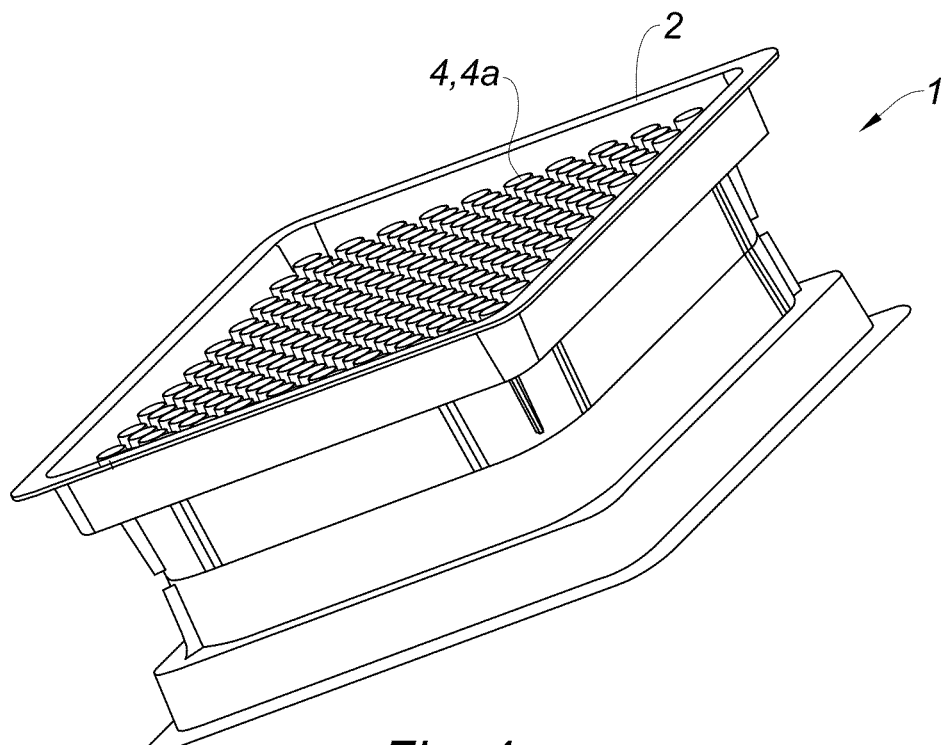
Figure 5:
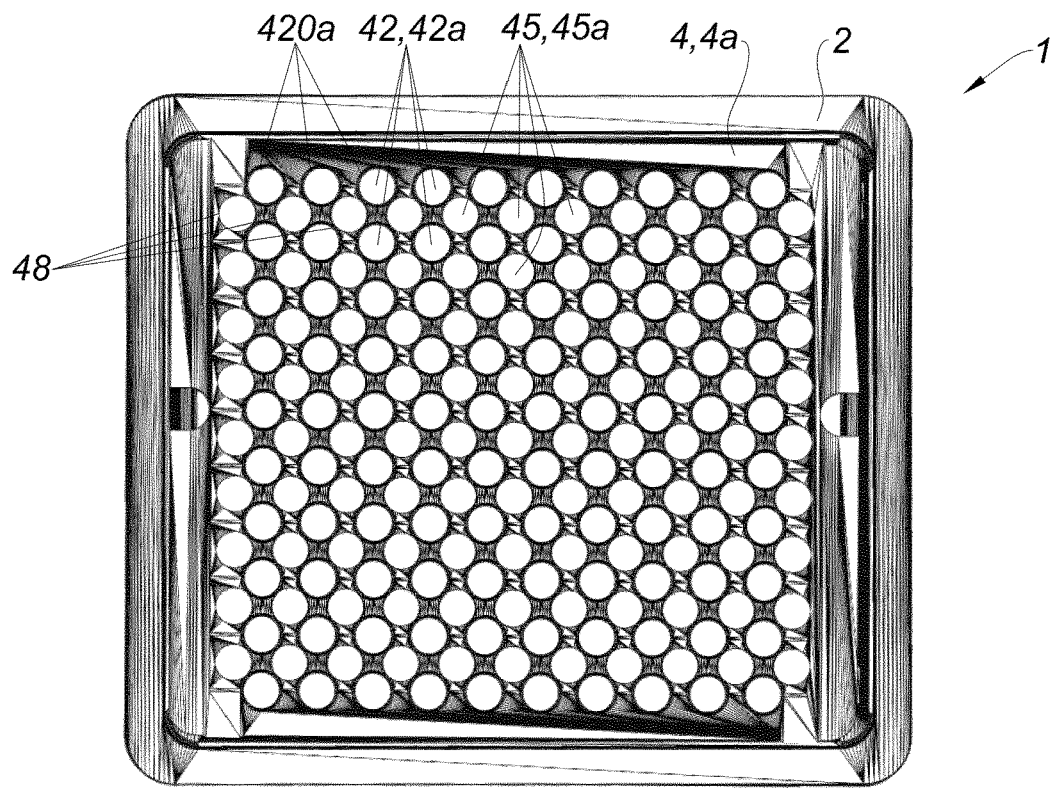
FIGS. 5 and 6 are top views of a packaging device according to an embodiment of the invention.
Figure 6:
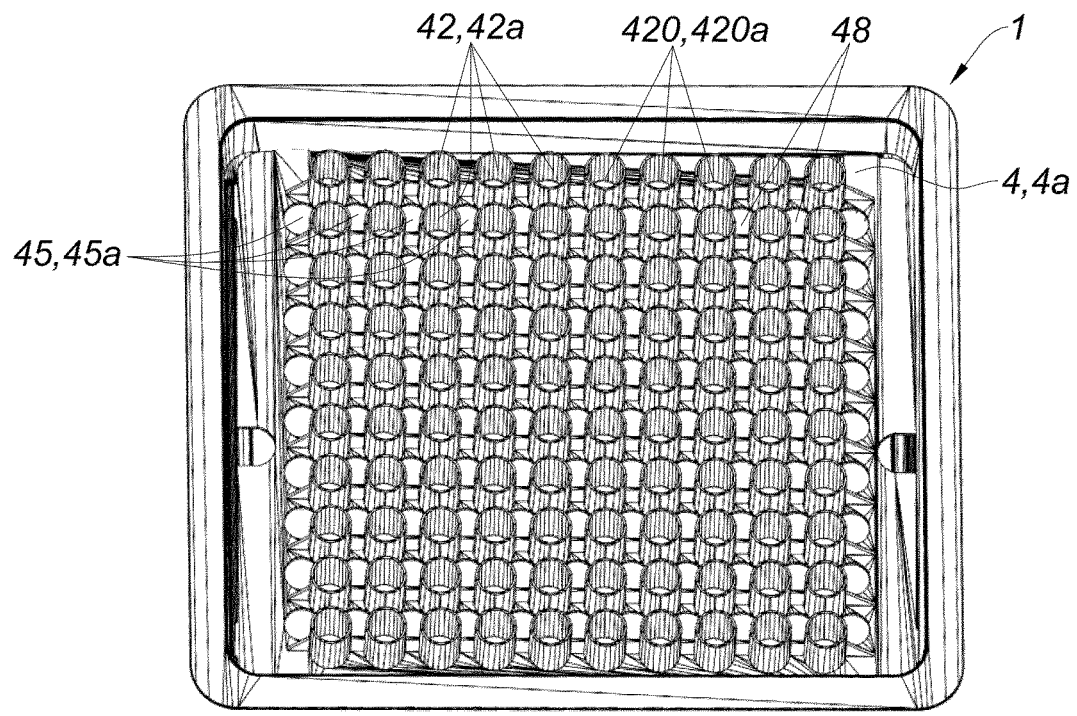
Figure 7:
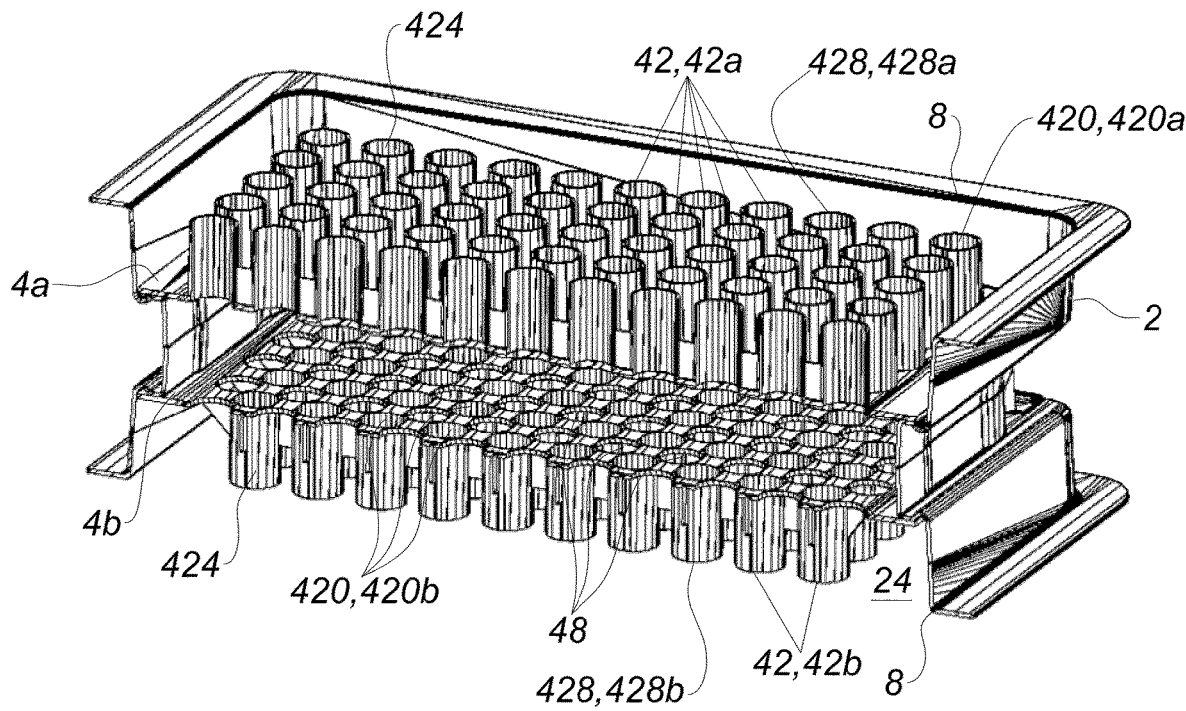
FIGS. 7 and 8 are cross section views of a packaging device according to an embodiment of the invention.
Figure 8:
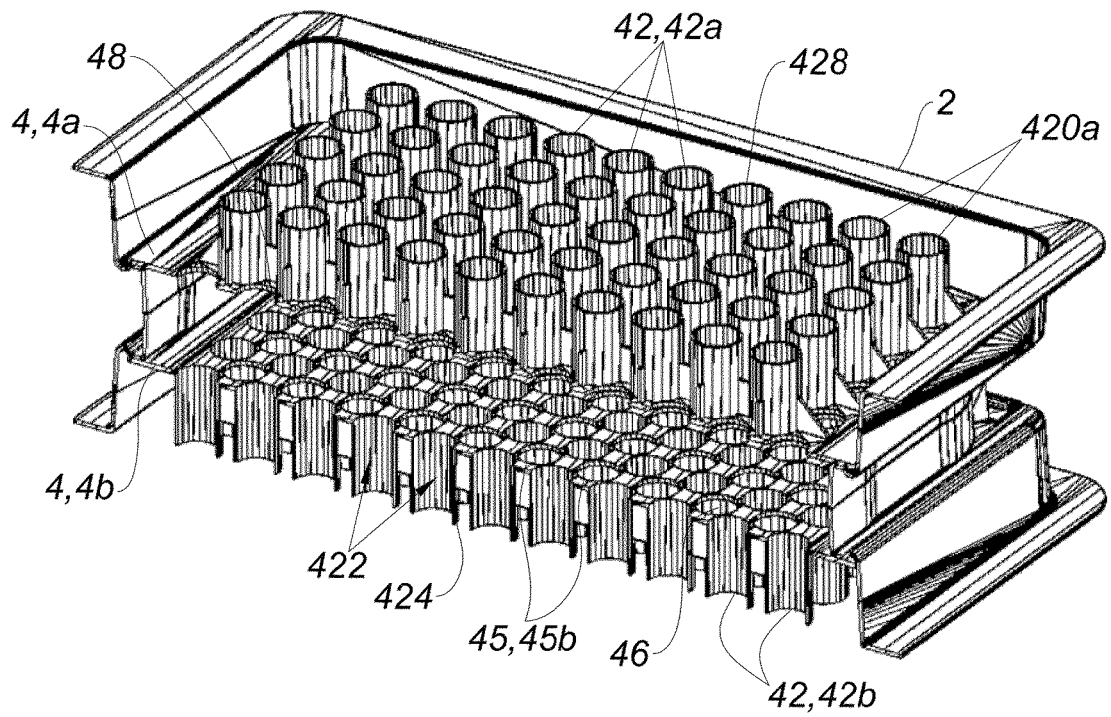
Figure 10:
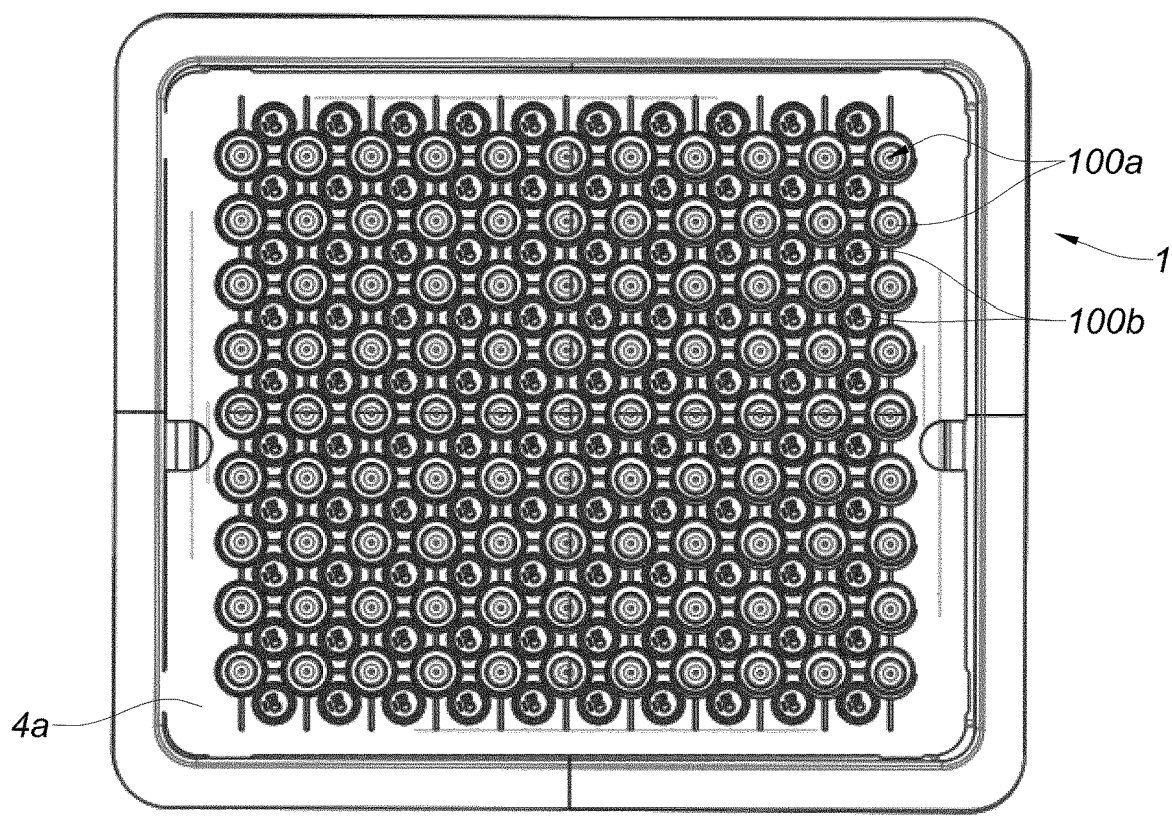
FIG. 10 is a top view of a packaging device according to an embodiment of the invention.
Figure 11:
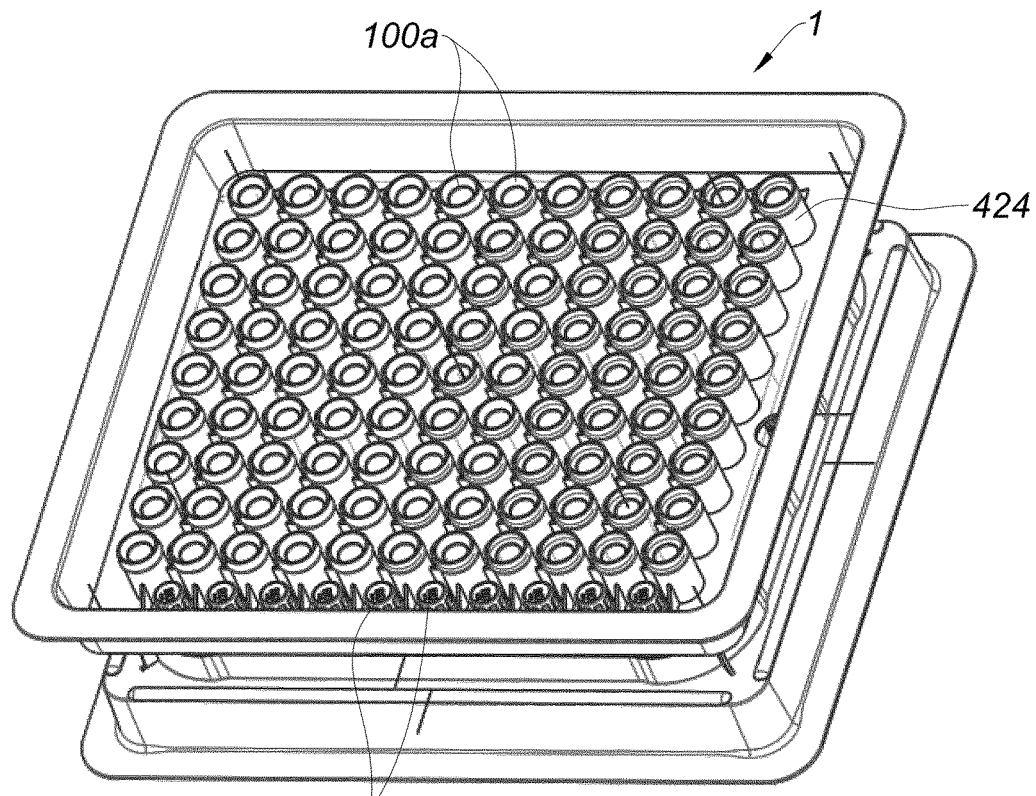
FIG. 11 is a perspective view of a packaging device according to an embodiment of the invention.

The method may comprise a first step of removing a first one of the two sealing elements 6 so as to open a first of the two openings 8 (FIG. 2A), for example by peeling off the sealing element 6 from the attachment surface 26. The method further comprises a second step of removing a first plurality of medical containers 100 supported by the nest 4a which faces the opened first opening 8. The removal of this first plurality of medical containers 100 may correspond to a removal of the nest 4 itself, as shown on FIGS. 2B and 2C. This removal may be operated by a translational movement of the nest 4 along the longitudinal axis A. The method may then comprise a third step of rotating the housing 2 according to a 180° rotation (FIG. 2D). The method may then repeat the same above mentioned first, second and third successive steps so as to remove the second plurality of medical containers 100, that is to say a step of removing the remaining sealing element 6 so as to open the second of the two openings 8 for example by peeling off the sealing element 6 from the attachment surface 26 (FIG. 2E) and a step of removing the remaining plurality of medical containers 100, for instance by removing the remaining nest 4 itself, said remaining nest 4 being removed by means of a translational movement along axis A and through said second extraction opening (FIG. 2D). The medical containers 100 may then be filled with a medical agent, before replacing the first nest 4a holding the medical containers 100a and/or the second nest 4b holding the medical containers 100b into the housing 2 for storage.

If the packaging device 1 comprises a single opening 8 configured to allow insertion or removal of the nests 4, the method may comprise a first step of removing a sealing element 6 so as to open this opening 8, for example by peeling off the sealing element 6 from the attachment surface 26. The method comprises a second step of removing the first plurality of medical containers 100 supported by the nest 4a which faces the opening 8. The removal of this first plurality of medical containers 100 may correspond to a removal of the nest 4a itself. This removal may be operated by a translational movement of the nest 4a along the longitudinal axis A. The method may then comprise a third step of rotating the second nest 4b, more precisely a step of rotating the housing 2, according to a 180° rotation. The method may comprise a fourth step of removing the housing 2 itself, for example by means of an upper translational movement of the housing 2 along axis A, so as to let the second nest 4b pass through the opening 8 and then allow removal of the medical containers supported by said second nest 4b. Alternatively, after having rotated the second nest 4b or the housing 2, the method may comprise removing a sealing element 6 so as to open a secondary aperture, said secondary aperture facing said second nest 4b and being smaller than the opposite opening 8 (said secondary aperture may face the second nest 4b but does not allow passage of the second nest 4b there through; the secondary aperture may however be dimensioned so as to permit removal of the medical containers supported by the second nest 4b). The method may then comprise a step of removing the remaining plurality of medical containers 100 without removing the second nest 4b, for example by means of a translational movement of said medical containers 100 along axis A and through said secondary aperture. The medical containers 100 may then be filled with a medical agent, before replacing the first nest 4a and/or the second nest 4b into the housing 2 for storage.

If the packaging device 1 comprises a spacer arranged between the first nest 4a and the second nest 4b in order to maintain a predetermined distance between these two nests 4a, 4b, then the method may comprise a step of removing this spacer from the housing 2. For example, said spacer may be removed before removal of the second nest 4b.

It is contemplated that removal of the medical containers 100 outside the housing 2 may be performed by the only removal of these medical containers 100, without removal of the nests 4 supporting these medical containers from the housing 2.

The invention claimed is:

1. A packaging device configured to support medical containers, the packaging device comprising:
   a first nest and a second nest,
   wherein said first nest including a first set of supporting units configured to support a proximal end of a first plurality of medical containers and said second nest including a second set of supporting units configured to support a proximal end of a second plurality of medical containers,
   the first set of supporting units and the second set of supporting units are configured to support said first plurality of medical containers and said second plurality of medical containers so that the first plurality of medical containers and the second plurality of medical containers are supported in an inverted position relative to each other, and
   the first nest comprises apertures configured to receive and maintain a distal end of the second plurality of medical containers while the second nest comprises apertures configured to receive and maintain a distal end of the first plurality of medical containers.

2. The packaging device according to claim 1, wherein the supporting units of said first set of supporting units delimit first apertures, each of said first apertures being configured to receive one medical container of said first plurality of medical containers, and the supporting units of said second set of supporting units delimit second apertures, each of said second apertures being configured to receive one medical container of said second plurality of medical containers, and said first apertures being arranged in staggered rows relative to said second apertures.

3. The packaging device according to claim 1, wherein the apertures comprise slanted walls configured to guide said distal ends inside the apertures.

4. The packaging device according to claim 1, wherein the supporting units each comprise a guiding conduit comprising a sidewall.

5. The packaging device according to claim 4, wherein the guiding conduits each delimits at least one slit.

6. The packaging device according to claim 4, wherein the guiding conduit has a polygonal shape.

7. The packaging device according to claim 4, wherein adjacent guiding conduits have a shared lateral wall portion.

8. The packaging device according to claim 4, wherein the guiding conduits have one end provided with a first aperture and an opposite end provided with a second aperture.

9. The packaging device according to claim 4, wherein the guiding conduit has a hexagonal shape.

10. The packaging device according to claim 1, wherein the packaging device comprises at least one sealing element configured to close the packaging device in order to keep sterility of a volume configured to contain the medical containers, and said at least one sealing element being permeable to a sterilization gas.

11. The packaging device according to claim 1, wherein the packaging device comprises:
   a housing delimiting an internal volume, the two nests being located inside the housing, and
   at least one opening leading into the internal volume, said at least one opening being configured to allow insertion or removal of at least one of the two nests inside or outside the housing.

12. The packaging device according to claim 1, wherein the packaging device comprises keyed elements configured to allow a single predetermined positioning of the nests relative to each other.

13. The packaging device according to claim 1, wherein the first nest and the second nest are molded in a single piece.

14. The packaging device according to claim 1, wherein the packaging device comprises:
   a housing delimiting an internal volume, the two nests being located inside the housing, and
   a first opening in the housing leading into the internal volume and a second opening in the housing leading into the internal volume, the first opening and the second opening being configured to allow insertion or removal of one of the two nests in to or out of the housing,
   wherein the first opening is on an opposite side of the housing from the second opening.

15. The packaging device according to claim 1, wherein the first nest is separated from the second nest.

16. The packaging device according to claim 1, wherein the first set of supporting units is provided in rows and the second set of supporting units is provided in rows and the rows of the first set of supporting units and the rows of the second set of supporting units are offset such that longitudinal axes of the first plurality of medical containers in a row of the first set of supporting units are offset from longitudinal axes of the first plurality of medical containers in a row of the second set of supporting units.

17. The packaging device according to claim 1, wherein the apertures in the first nest are provided in a space between at least two supporting units of the first set of supporting units and the apertures in the second nest are provided in a space between at least two supporting units of the second set of supporting units.

18. The packaging device according to claim 1, wherein the first nest is a first planar support plate, the second nest is a first planar support plate, and longitudinal axes of the first plurality of medical containers and the second plurality of medical containers extend perpendicular to the first planar support plate and the second planar support plate.

19. A method for removing the pluralities of medical containers from the packaging device according to claim 1, comprising the steps of:
   removing the first plurality of medical containers supported by the first set of supporting units outside the packaging device,
   turning the packaging device over, and
   removing the second plurality of medical containers supported by the second set of supporting units.

* * * * *

UNITED STATES PATENT AND TRADEMARK OFFICE
CERTIFICATE OF CORRECTION

| | |
|---|---|
| PATENT NO. | : 11,547,631 B2 |
| APPLICATION NO. | : 16/652792 |
| DATED | : January 10, 2023 |
| INVENTOR(S) | : Lionel Maritan et al. |

It is certified that error appears in the above-identified patent and that said Letters Patent is hereby corrected as shown below:

On the Title Page

Item [57], Line 1, after "device" delete "is"

Item [57], Lines 8-9, delete "maintainer" and insert -- maintain --

Signed and Sealed this
Seventh Day of March, 2023

Katherine Kelly Vidal
*Director of the United States Patent and Trademark Office*